United States Patent [19]

Erikson

[11] 3,990,296
[45] Nov. 9, 1976

[54] ACOUSTICAL HOLOGRAPHY IMAGING DEVICE

[75] Inventor: Kenneth R. Erikson, South Laguna, Calif.

[73] Assignee: Actron, a Division of McDonnell Douglas Corporation, Monrovia, Calif.

[22] Filed: Jan. 8, 1975

[21] Appl. No.: 539,316

[52] U.S. Cl. .............................. 73/67.5 H; 128/2 V; 340/5 H
[51] Int. Cl.² .......................................... G01N 29/04
[58] Field of Search .................. 73/67.5 H, 67.5 R; 340/5 H, 5 MP; 128/2 V

[56] References Cited
UNITED STATES PATENTS

| | | | |
|---|---|---|---|
| 3,533,056 | 10/1970 | Clark | 340/5 H X |
| 3,711,823 | 1/1973 | Green | 73/67.5 H X |
| 3,745,812 | 7/1973 | Korpel | 73/67.5 H X |
| 3,890,829 | 6/1975 | Korpel | 73/67.5 H |

Primary Examiner—Richard C. Queisser
Assistant Examiner—John P. Beauchamp
Attorney, Agent, or Firm—Kleinberg, Morganstern, Scholnick & Mann

[57] ABSTRACT

An acoustical imaging system wherein an acoustic beam projected through a transmission medium is modified (scattered) by a subject therein and impinges upon one side of an acousto-optic interface. The other side of this interface is made concave and mirror-surfaced to reflect an illuminating laser beam. The acousto-optic interface is "composite," being fabricated from an epoxy matrix with a multitude of tiny spherular capsules, or "microballons" distributed therein to thereby match the acoustic impedance of this interface to that of the transmission medium.

15 Claims, 2 Drawing Figures

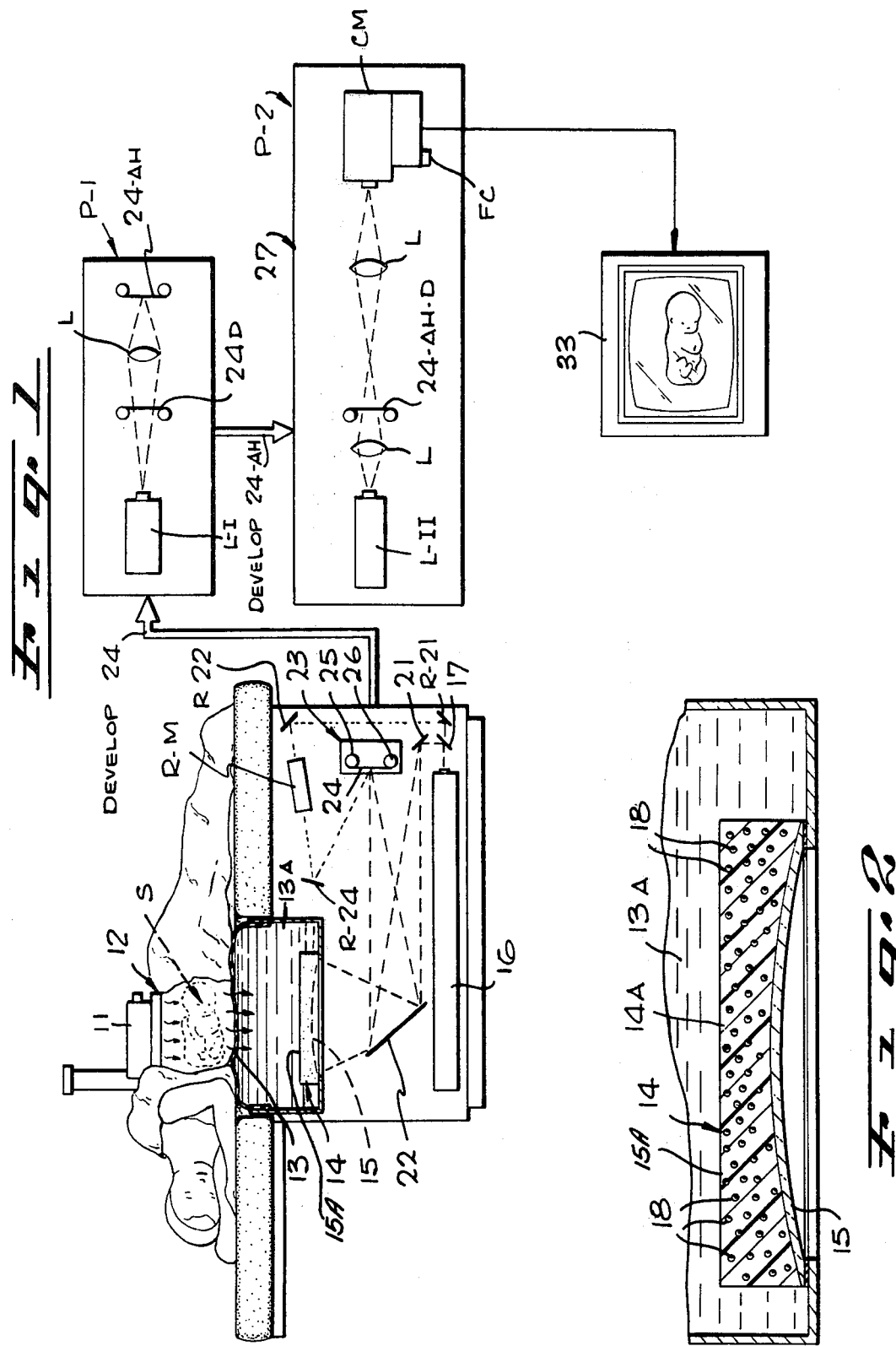

ACOUSTICAL HOLOGRAPHY IMAGING DEVICE

BACKGROUND OF THE INVENTION

1. Field of the Invention

The present invention relates to acoustical ultrasonic imaging and acoustical holography and, more particularly, to an improved acousto-optic interface enabling photographic recording of the effect of an acoustic wavefront on the interface.

2. Description of the Prior Art

High frequency sound readily travels through comparatively dense homogenous substances, such as liquids or solids. A "test subject," whose internal structure is to be studied (exemplarily, a portion of the human body as described here), may be illuminated by an acoustic wave and the wave modulation studied as a representation of the subject. This subject should be coupled to a sound source, through a liquid medium having an acoustic impedance close to that of the subject.

Water is a convenient form of such a coupling liquid for study of a human subject. When an acoustic wavefront is scattered by somatic tissue and continues, through a water medium, to impact an acousto-optic interface, it can so distort the interface as to form a ripple pattern representing the character of the target tissue. Detection and recording of this distortion can provide a useful representation of the body.

Ultra-sound energy (circa 0.4–20 MHz range) is useful for such diagnostic purposes such as penetrating and imaging soft tissue (especially "in vivo", such as a human foetus in situ, i.e., within the mother's womb), being fluid coupled between an appropriate sound-source transducer and a detection or imaging arrangement. Mechanical scanning systems, commonly known as B-Scan systems are well known to workers in the art and are commonly used in hospitals. These manual systems map a plane of the subject point by point and are slow and require highly trained operators. Newer systems use imaging techniques in which a plane or large volume of the subject are interrogated simultaneously. For instance, in systems like those contemplated by the subject invention, a relatively large, three-dimensional volume (e.g., a cylinder 30 centimeters in diameter by 30 centimeters high), may be imaged with relatively high resolution (on the order of a few millimeters) and using a single, short burst of ultra-sound, on the order of one to several microseconds long.

Such systems can avoid the deleterious effects of subject movement, need no acoustic lenses or scanning devices and apply relatively low average acoustic power. Such systems will be understood by workers in the art to facilitate image generation with greater ease and reliability and not require highly trained technicians. Additionally, a permanent hoolographic film record may be obtained for later viewing and study. Such a hologram also allows a radiologist to focus upon different depths of the test subject. Such a technique is harmless, non-invasive, and non-ionizing, yet is relatively cost-effective and useful for obtaining holographic images of soft tissue structures and organs in human and animal bodies.

A variety of acousto-optic interfaces have been proposed to facilitate recording of scattered acoustic waves. Exemplarily, an oil film on the surface of a water medium might be used; but this is not practical since oil films are very sensitive to vibration and have poor reflectivity. Another interface suggested is a thin plastic film on the surface of a coupling fluid. Thin films are less sensitive to vibration, but their reflecting qualities are nonetheless generally poor. Relatively thicker plastic plates would be conceivable except that they cannot be readily provided with a good optical finish; also, they offer a relatively poor acoustic impedance match with a water medium, causing reflection and a loss of sound energy.

Acousto-optic interfaces heretofore considered in the prior art are, theerefore, not generally satisfactory. Further, when employing acoustical techniques for diagnostic investigation of portions of a human subject it is usually desirable to place the acousto-optic interface below the patient. Obviously, oil films and thin plastic sheets cannot be employed as the interface in such cases, while the thicker plastic sheets will divert too much sonic energy, as well as not accommodating a suitable optical finish.

At (acoustic vibration) frequencies near 1 MHz a large aperture system is needed for medical imaging purposes to provide adequate resolution for reasonably large volumes (e.g., that of the human abdomen). For instance, the system of FIG. 1 would typically use a 30 cm diameter flat acousto-optic interface with a high quality imaging lens. Fabricating a high quality Fourier transform lens of that diameter is a formidable, expensive undertaking. These difficulties are avoided by fashioning a concave-mirror interface according to the invention.

SUMMARY OF THE INVENTION

It is highly desirable that the maximum acoustic energy be coupled through an acousto-optic interface. This affords maximum contrast in the pattern rendered on the interface. It is also desirable, for compactness and efficiency, to provide a concave reflective mirror along the optical path of the illumination directed upon the interface in place of the lens as heretofore employed.

According to the present invention, aa novel acousto-optic interface is provided which has a concave, optically "convergent" face and, according to a second feature, is comprised of "composite" material, selected to yield a resultant acoustic impedance matched to that of the acoustic media.

The acoustic-optic interface transforms the acoustic field scattered by the insonified subject into time-varying displacements on the optical quality interface surface, these displacements being detected with coherent illumination generating holographic images on motion picture film.

Other features, objects and advantages of the present invention will become more apparent by referring to the following specification and accompanying drawings.

BRIEF DESCRIPTION OF THE DRAWINGS

FIG. 1 illustrates an acoustic holographic arrangement employing an acousto-optic interface according to the present invention together with image development and projection means; and FIG. 2 is a cross-sectional view of a preferred embodiment of an improved acousto-optic interface according to the present invention.

DESCRIPTION OF PREFERRED EMBODIMENTS

Referring now to FIG. 1 of the drawings, an ultrasonic source 11 is provided, here being understood as comprising a piezoelectric device driven at MHz frequencies (1 MHz preferred here), as known in the art. Source 11 is coupled to a prescribed "subject volume" S (here, the midsection of a human patient) via a water-filled bag 12, or like sonic coupling means.

The illuminating ultrasonic waves from source 11 are scattered by body tissue of varying densities and resiliencies, etc. as well known in this art to develop an acoustic "imaging wave." These scattered waves are coupled, through the relatively transparent transmission media, to the detecting interface 14. Here, the transmission media exemplarily comprise an approximate continuum of liquid acoustic conductor means; namely, a water-filled bag 13 and an associated water-filled detection chamber 13-A. Bag 13 may conveniently take the form of a water-filled flexible cushion, similar to a water bed, as illustrated in FIG. 1, and bag 13 may form the top enclosure of chamber 13-A as also illustrated in FIG. 1. Chamber 13-A may preferably take the form of a rigid-wall tank filled with water and relieved on one side to accomodate the acousto-optic interface 14, attached thereto in water-tight fashion.

The sound waves from source 11 are thus transmitted through bag 12, scattered by subject S, and then traverse the liquid media, being passed by the liquid contained by bag 13 of chamber 13-A, to finally impinge on interface 14. The scattered waves traverse the upper face 15-A of interface 14 and appear as a pattern of "ripples" on the lower, reflecting "detection face" 15 of interface 14.

This ripple pattern appearing upon detection face 15 is to be optically detected and recorded according to known techniques. Face 15 is, according to the invention, preferably formed into a spherical concave mirror adapted to reflect and focus incident radiation as known in the optical arts. Interface 14 is constructed of composite material, having a cross-sectional thickness which is relatively large compared with the wave-length of the transmitted sound waves; for example, being almost an inch thick here. The material forming interface 14 is selected and arranged to be readily deformed by these waves. (See below). The optical quality mirror surface on face 15 may be conventionally rendered, such as by electroplating and polishing, or, more preferably, by means of optical replication.

A coherent light souorce and associated optical directing, controlling and recording means are contemplated for optically detecting and holographically rendering the "acoustic ripple pattern" and associated holographically encoded "acoustic image" on face 15. This will represent the character of the subject S as known in the art. Here, the illumination source preferably comprises a pulsed laser 16 (e.g., Xenon gas laser) arranged to provide a pulsed beam, which is split, conventionally, into an "object beam" (dashed line FIG. 1) and a "reference beam" (dotted line). These beams interfere to form a hologram of the ripple pattern on film 24, as known in the art.

More particularly, the object beam is directed onto detection face 15 (via beam splitter 17 and mirrors 21 and 22) to be focused thereby (see below) and reflected back, via mirror 22, onto recording film 24. The reference beam (dotted line) is presented to form the optical hologram on film 24, as known in the art, being passed through beam splitter 17 and reflected by mirrors R-21, R-22, and R-24. This reference beam is also phase-modulated in a prescribed manner to simulate "reference" acoustic waves and so develop an acoustic hologram, as known in the art. e.g., see discussion in "Linearized Subfringe Interferometric Holography," by A. F. Metherell, in Acoustical Holography Vol. 5, Ed. P. S. Green, Plenum, N.Y., N.Y. 1974. Modulator means R-M modulates the reference laser beam at the frequency of the ultra sound source, to enable production of the acoustic hologram on film 24, along with the optical hologram. This dual hologram is later developed and viewed (See below).

The concave mirror surface 15 of interface 14 will be seen, according to this feature, to enhance such optical detection and recording of the ripple pattern. That is, the laser object beam illuminates the surface displacements, or ripples, produced upon detection face 15 by the ultra sound wave imaging-volume S, as transmitted through the water media. This ripple pattern can, in an alternative embodiment, be otherwise arranged to render the acoustic hologram on face 15 directly, i.e., by the contemporaneous application of a reference ultrasound wave thereto (through the liquid medium, but unaffected by subject S) as known in the art. — i.e., avoiding the mentioned phase modulation of the reference beam. But such a reference sound is here simulated by, instead, modulating the reference laser beam with this ultra-sound frequency. Conveniently, recording camera 23 may comprise a conventional 16 mm motion picture camera without a lens, presenting frames (photographic film strips) 24 in sequence (i.e., advancing them for exposure, between supply reel 25 and storage reel 26, as known in the art). Each frame is synchronized with the generation of one subject ripple pattern and associated laser pulse. The reference beam phase-modulation is taken, preferably from the same oscillator that drives ultrasonic source 11. The image recorded on film 24 will be understood to comprise both an optical hologram and a true acoustic hologram that may be recorded and read-out by means known in the art and described below.

INTERFACE DETAILS

An enlarged cross-sectional view of the acousto-optic interface 14 is illustrated in FIG. 2. The interface body 14-A is fabricated of material selected to be a relatively close "match" in acoustic impedance to the liquid media for the contemplated arrangement. Here, it is preferred to use a "gas-filled polymeric" or like composite material preferably comprising an epoxy matrix together with "acoustically-transparent" spherular material. The "gas-filled" epoxy embodiment illustrated has a great number of spherular gas-filled capsules, or glass microballoons, 18 distributed relatively uniformly throughout its cross-section. These microballoons comprise tiny hollow glass beads, or glass-walled bubbles, filled with air or a like low-density gas — whose low density and small size make it transparent to the contemplated sound. By selection of such a gas-filled epoxy material, the overall acoustic impedance of the interface 14 is controlled so as to be equal, or close, to that of the coupling liquid; thereby enabling it to transmit the contemplated acoustic waves from the fluid medium 13A into the interface body 14-A, thus traversing face 15A substantially undistorted.

Microballoons 18 are selected to have a diameter substantially less than the contemplated acoustic wavelength (here a 25 micrometer diameter is used with 1 MHz ultrasound which has a wavelength in water of about 1.5 millimeters.) With the acoustic impedance of the interface so matched to that of the coupling water medium, the sound waves transmitted will be understood as efficiently coupled from fluid medium 13 A to detection surface 15 with no significant reflections or associated energy loss (as typically results at the interface between media of different effective acoustical impedances.) Here, the epoxy matrix will be recognized as having a density much greater than water (which is 1.0); while the micro-capsule filling has a much lower density. The volume distribution of these capsules is such as to create an effective, composite interface density reasonably close to unity. The microballoons, being considerably smaller than the contemplated acoustic wavelength, do not impair transmission, yet they serve to modify the composite, overall density of the interface body 14-A to be matched to the acoustic transmission medium.

The relationship required for such "equalized" acoustic impedances ($z$) may be expressed as:

$$Z = \rho_i C_i = \rho_W C_W$$

where:

$\rho_i$ is the (overall) density of interface 14;
$C_i$ is the velocity of sound in interface 14;
$\rho_W$ is the density of water or other fluid coupling medium 13A; and
$C_W$ is the velocity of sound in water or other fluid coupling medium.

Water has a $Z_W$ of about $1.5 \times 10^6$ (1500 m/sec $\times$ 1.0 $\times 10^3$ Kg/m$^3$) and in epoxy it may be taken to have a $Z_e$ of about $2.9 \times 10^6$ (2200 m/sec $\times$ 1.3 $\times 10^3$ Kg/m$^3$). Thus, the concentration and density of the low-mass filling should be such as to bring the overall interface impedance $Z_i$ close to $1.5 \times 10^6$, as workers will understand.

Such spherule-filled epoxy material with the internally distributed glass microballoons is commercially available; for instance as "XP-241 Syntactic Foam" (from 3M Company). Other syntactic foam materials having the properties described may be employed. Syntactic foam is defined by the American Society for Testing Materials as "a material consisting of hollow sphere fillers in a resin matrix."

Workers will recognize that the epoxy matrix, may be otherwise modified to derive an overall reduction in composite density using other "low-density", microdiameter "filler" material, selected and homogeneously dispersed throughout the matrix so as to yield the desired composite; this filler also being acoustically transparent and not adversely affecting transmission of the contemplated sound waves. Workers will visualize such modifications; for instance by introducing tiny, uniform, small diameter, gas bubbles into a heavier matrix (e.g., tiny bubbles blown with Freon or a like blowing agent into a matrix like urethane foam), or by introducing similar spherules of low-density material, such as gas-filled plastic spheres or spheres of very lightweight material.

Likewise, workers will recognize that the epoxy matrix may be substituted for with another "visco-elastic" material giving good acoustic response (e.g., a glass sheet) and also accepting an impedance-matching filler like the tiny microballoons, like gas bubbles, etc. Workers will recognize such visco-elastic material as being truly elastic under the impact of acoustic waves. Materials like glass will be superior to polymers like epoxy for certain purposes, e.g., at higher acoustic frequencies.

As illustrated in the drawings, the optical face 15 of interface 14 preferably takes the form of a concave semi-spherical mirror adapted to function as a good optical quality reflector on which a ripple pattern may be detected. That is, the interface will act as a free boundary surface, converting the scattered acoustic field into a time-varying displacement pattern on its face with the amplitude and phase of this pattern proportional to those of the incident acoustical field. The composite epoxy body is an excellent substrate for forming a converging high quality optical mirror (e.g., by replication methods. As is well known in the art, a mirror replica may be fabricated thereon by coating a thin layer of epoxy on the interface substrate and affixing an additional layer thereon, the latter being cast in contact with a high quality optical surface. The thin reflecting layer of epoxy so formed is then metalized to form the mirror. Alternatively, conventional plating or polishing methods may be employed to provide the needed high quality mirror surface as known in the art.

PROCESSING OF "RIPPLE IMAGE" RESULTS

The acousto-optic interface of the present invention receives the ultrasonic wave pattern, as modified by the object under study in the water medium, and presents it as a ripple pattern to be optically detected and recorded.

As mentioned, the sound waves causing the minute surface displacements (ripple pattern) on the interface represent the tissue under study. This displacement pattern is, preferably, recorded, using a pulsed laser holographic system with special conversion and recording techniques as described below. There is, of course, no substantial reflection of this ultrasonic wave during transmission, since all acoustical-impedance anomalies in the media are minimized or avoided according to the invention. The medium thus exhibits high acoustic efficiency for high quality acoustic holography. This ripple pattern when illuminated by appropriate coherent radiation (laser beams) may be recorded, as an optical hologram as mentioned. The concave shape and related coupling properties of the detection face provided according to the invention act to project a good optical image of the acousto-holographic pattern thereon.

More particularly, a movie of successive "double-holograms" is made, synchronizing the ultra-sound burst with frame advancement. The movie film may be developed, using conventional film processing, into a series of optical holograms; and then reconstructed as the ripple patterns and imaged onto another film and developed to form acoustical holograms. The acoustical holograms are, in turn, reconstructed and viewed, to thus represent images of the insonified structure (here a foetal subject in the patient's body) as "seen" by the sound wave. This film can, of course, be viewed at any time and the viewing physician can focus on any plane of the "insonified" zone. Since the film is a motion picture (series of "still" frames, rapidly scanned), the physician may also view relatively slow organ motion as well as static subjects. We will consider in more detail the general process of developing of the image in which the film 24 directly imaging the interface is developed and then "projected" with a laser to reconstruct the holographic movie frames onto a second viewing film strip to be used to develop an acoustical holographic movie.

DEVELOPMENT PROCESS — PARTICULAR EXAMPLE

More particular image processing details, representing a preferred implementation, will now be described. Film 24 comprises 16 mm movie film (or like large-area film) and is processed in the normal manner and, as developed (film 24-D), will represent a set of optical holograms of acousto-optic interface surface 15. Here a conventional "wet development" may be undertaken, preferably with a conventional motion picture film processor, somewhat modified. For example, the 16 millimeter "Recordak Prostar Processor" (tradename of Kodak Company) may be used. Alternatively, holograms may be imaged and developed with any other comparable technique, such as electro-graphically (e.g., Xerography), thermographically, using photo polymers, dry process film, etc.

Developed film 24-D is then illuminated by a "Development laser" L-I (preferably a low power He-Ne gas laser) as part of a "wave-front reconstruction" process regime P-1 (FIG. 1). The holographic image so reconstructed with laser L-I, plus a suitable associated optical system (as well known in the art), is used to develop an acoustic-hologram on a second film strip 24-AH, preferably on "Super-8" film (or other reduced-area, available film) so as to "shrink" the (16 mm) original image and counteract the tendency of the laser projection system to "stretch" images and distort them. According to this feature, a 12 inch diameter ripple pattern is thus reduced about 48 × (to ¼ inch) with good results. Thus, the original optical hologram (i.e., with the usual optical amplitude and phase information) is reconstructed to form the acoustical hologram on the second (viewing) film; with this viewing film being optically reconstructed by the viewer into an image of the patient's organs so insonified. Film 24 -AH is then developed conventionally (as above with film 24-D) to form viewing movie strip 24-AH-D which is sent to a second ("viewing") regime P-2, to be laser-reconstructed for viewing. At P-2, film 24-AH-D is illuminated by a second, "viewing" laser L-II (preferably a low-power He-Ne laser) and projected through focusing lenses to a TV camera CM, to be viewed at an associated TV monitor 33 connected to the camera output. By controlling the plane of focus of the television camera (e.g., with focus control FC) cross-sections of the subject as insonified (see foetus image at receiver 33), may be focused-upon at different depths, being selected and controlled by known means. Thus, the acoustical holograms being reconstructed to yield a movie of the insonified volume as "seen" by the ultrasound.

In principle, the acoustical hologram could be reconstructed from the optical hologram in one step; however, in practice, because of a "non-ideal mirror" surface on the interface and because of low holographic efficiency, two reconstruction steps are described and preferred.

Other embodiments of the present invention and modifications of the embodiments presented herein may be developed without departing from the essential characteristics thereof. Accordingly, the invention should be limited only by the scope of the claims appended below. For instance, lasers and holography may, in certain cases, be dispensed with and the interface otherwise illuminated, detected and imaged or recorded (e.g., with ordinary "white" light). Or, the laser read-out may instead take the form of a laser raster scan of the interface so as to otherwise register the displacement pattern, as known in the art. The acoustic (ultra sound) transparency and good impedance match (to medium) of the interface will still afford a better, more representative ripple pattern; also, its concavity and associated optical focusing capability will nonetheless be useful to generate holographic image in a single, cost-effective manner. Similarly, other, high frequency sound may be transmitted through such an improved interface, the low-density sites being small enough and light enough to be relatively transparent to this sound.

Likewise, such an improved interface may be employed with other acoustic imaging systems or other systems arranged to transduce sound waves or to focus them, as an improved acoustic lens.

What is claimed as new and patentable is:

1. In an ultrasonic acousto-optical imaging arrangement, an improved acousto-optic interface structure arranged to couple acoustical information in a prescribed liquid medium efficiently to a prescribed gaseous medium, said structure comprising:

a body having a first face adapted for contacting said liquid medium and a second face, disposed opposite said first face and adapted to contact said gaseous medium, said second face being curved into a concave outward configuration to reflect and focus prescribed incident radiation in a prescribed manner, whereby a surface-displacement representation of the scattered wave disturbances is formed;

said body being adapted to be agitated by ultrasonic wave disturbances scattered and transmitted through said liquid and, in response to these wave disturbances, to develop a ripple pattern on said second face faithfully representing the wave disturbances;

said body being composed of a composite material comprising at least one high density material having an acoustic impedance substantially higher than that of said liquid medium, and of at least one low density material having an acoustic impedance substantially lower than that of the liquid medium, said low density material being dispersed uniformly throughout said high density material to achieve a net acoustic impedance for said body substantially matched to that of the liquid medium.

2. In an ultrasonic acousto-optical imaging arrangement, an improved acousto-optic interface structure arranged to couple acoustical information in a prescribed liquid medium efficiently to a prescribed gaseous medium, said structure comprising:

a body having a first face adapted for contacting said liquid medium and a second face, disposed opposite said first face and adapted to contact said gaseous medium;

said second face being curved into a concave outward configuration to reflect and focus prescribed incident radiation in a prescribed manner, whereby a surface-displacement representation of the scattered wave disturbances is formed;

said body being adapted to be agitated by ultrasonic wave disturbances scattered and transmitted through said liquid and in response to these wave disturbances, to develop a nipple pattern on said second face faithfully representing the wave disturbances;

said body being composed of a composite material comprising a matrix of high density material throughout which gaseous void sites are homogeneously dispersed to impart to said body an acoustic impedance substantially equal to that of the liquid medium.

3. The interface structure as recited in claim 2 wherein said high density material comprises a synthetic polymeric foam matrix material and gaseous void sites are relatively uniformly dispersed throughout, said void sites being small enough to be relatively transparent to, and avoid any substantial interference with, transmission of said sound waves.

4. The interface structure recited in claim 3 wherein said matrix material comprises a syntactic foam.

5. In an ultrasonic acousto-optical imaging arrangement, an improved acousto-optic interface structure arranged to couple acoustical information in a prescribed liquid medium efficiently to a prescribed gaseous medium, said structure comprising:

a body having a first face adapted for contacting said liquid medium and a second face, disposed opposite said first face and adapted to contact said gaseous medium;

said second face being curved into a concave outward configuration to reflect and focus prescribed radiation in a prescribed manner, whereby a surface-displacement representation of the scattered wave disturbances is formed;

said body being adapted to be agitated by ultrasonic wave disturbances scattered and transmitted through said liquid, and, in response to these wave disturbances, to develop a ripple pattern on said second face faithfully representing the wave disturbances;

said body being composed of a composite material comprising a syntactic-foam polymeric matrix including a multiplicity of gaseous microballoons dispersed uniformly throughout to impart to said body an acoustic impedance substantially equal to that of the liquid medium.

6. The interface structure recited in claim 5 wherein said microballoons comprise thin glass spherules having a low mass gaseous filling and a diameter substantially less than the wavelength of said transmitted sound.

7. The interface structure recited in claim 2 wherein said matrix is comprised of epoxy material.

8. The interface structure recited in claim 2 wherein said matrix is comprised of a urethane material.

9. In an acoustical holography imaging system, the combination comprising:

ultrasonic sound generating means;

acousto-optic interface means arranged and adapted to receive sound waves generated by said generating means and to represent them in a prescribed ripple pattern;

said acousto-optic interface means comprising a body with a first, liquid-contacting surface and a second, gas-contacting surface;

said body being a composite material comprised of a high density visco-elastic matrix with low density, micro-diameter sites therein to efficiently and faithfully transmit said sound waves;

said second surface being curved into a concave-outward configuration to reflect and focus prescribed incident radiation in a prescribed manner;

liquid acoustic coupling means disposed between said sound generating means in said first interface surface and adapted to transmit prescribed ultrasonic vibrations efficiently thereto;

illumination means for directing prescribed radiation upon said second interface surface; and optical detecting means for detecting and recording illumination reflected from said second surface to thereby image said ripple pattern.

10. The combination as recited in claim 9 wherein said matrix is comprised of a polymeric and said sites comprise spherule gas microballoons with a diameter on the order of 1/50th or less of the acoustic wavelength in the medium.

11. In an acoustical holography imaging system, the combination comprising:

ultrasonic sound generating means;

acousto-optic interface means arranged and adapted to receive sound waves generated by said generating means and to represent them in a prescribed ripple pattern;

said acousto-optic interface means comprising a body with a first, liquid-contacting surface and a second, gas-contacting surface;

said body being composed of a composite material comprising first and second materials of different densities, said first material comprising a polymeric matrix and said second material comprising an array of low density sites substantially uniformly dispersed throughout said matrix, each site comprising a relatively small volume having a diameter substantially less than the wave length of the ultrasonic sound waves to be transmitted through said medium and said body, to efficiently and faithfully transmit said sound waves through said body;

said second surface being curved into a concave-outward configuration to reflect and focus prescribed incident radiation in a prescribed manner;

liquid acoustic coupling means disposed between said generating means and said first interface surface and adapted to transmit prescribed ultrasonic vibrations efficiently thereto;

illumination means for directing prescribed radiation upon said second interface surface; and optical detecting means for detecting and recording illumination reflected from said second surface to thereby image said ripple pattern.

12. The combination recited in claim 11 wherein said sites are comprised of relatively low density gas.

13. The combination as recited in claim 11 wherein said body comprises a syntactic foam having a plurality of microballoons dispersed throughout.

14. The combination as recited in claim 11 wherein each low density site comprises a gas bubble encapsulated in a glass spherule.

15. The combination as recited in claim 11 wherein said matrix comprises an epoxy foam.

* * * * *